United States Patent
Sherman

(10) Patent No.: US 10,744,156 B2
(45) Date of Patent: Aug. 18, 2020

(54) INTRADIALYTIC USE OF SODIUM THIOSULFATE

(71) Applicant: Hope Medical Enterprises, Inc., Scottsdale, AZ (US)

(72) Inventor: Craig Sherman, Scottsdale, AZ (US)

(73) Assignee: Hope Medical Enterprises, Inc., Scottsdale, AZ (US)

( * ) Notice: Subject to any disclaimer, the term of this patent is extended or adjusted under 35 U.S.C. 154(b) by 0 days.

(21) Appl. No.: 15/914,661

(22) Filed: Mar. 7, 2018

(65) Prior Publication Data

US 2018/0256639 A1    Sep. 13, 2018

Related U.S. Application Data

(60) Provisional application No. 62/468,871, filed on Mar. 8, 2017.

(51) Int. Cl.
*A61K 33/04* (2006.01)
*A61M 1/16* (2006.01)

(52) U.S. Cl.
CPC .......... *A61K 33/04* (2013.01); *A61M 1/1654* (2013.01); *A61M 1/1656* (2013.01)

(58) Field of Classification Search
None
See application file for complete search history.

(56) References Cited

U.S. PATENT DOCUMENTS

| | | | |
|---|---|---|---|
| 5,843,316 A | 12/1998 | Kurittu | |
| 7,022,315 B2 * | 4/2006 | Neuwelt | A61K 33/243 424/59 |
| 7,862,530 B2 * | 1/2011 | Callan | A61K 31/19 210/645 |
| 8,216,776 B2 | 7/2012 | Sakai et al. | |
| 8,496,973 B2 | 7/2013 | Sherman | |
| 8,568,793 B2 | 10/2013 | Sherman | |
| 8,715,746 B2 | 5/2014 | Sherman et al. | |
| 8,920,852 B2 | 12/2014 | Sherman et al. | |
| 9,144,580 B2 | 9/2015 | Sherman et al. | |
| 9,283,249 B2 | 3/2016 | Sherman et al. | |
| 9,345,724 B2 | 5/2016 | Sherman et al. | |
| 9,504,709 B2 | 11/2016 | Sherman et al. | |
| 9,579,345 B2 | 2/2017 | Sherman et al. | |
| 9,579,354 B2 | 2/2017 | Clements et al. | |
| 9,585,912 B2 | 3/2017 | Sherman et al. | |
| 9,687,505 B2 | 6/2017 | Sherman et al. | |
| 9,687,506 B2 | 6/2017 | Sherman et al. | |
| 9,944,524 B2 | 4/2018 | Sherman et al. | |
| 2004/0096845 A1 * | 5/2004 | Sakai | A61K 9/08 435/6.11 |

(Continued)

OTHER PUBLICATIONS

Ivankovich et al., "Sodium Thiosulfate Disposition in Humans: Relation to Sodium Nitroprusside Toxicity," Anesthesiology, 58(1):11-17, Jan. 1983 (Year: 1983).*

(Continued)

*Primary Examiner* — Chester T Barry

(74) *Attorney, Agent, or Firm* — Jones Day

(57) ABSTRACT

Provided herein are methods for maintaining physiological levels of thiosulfate in a subject undergoing hemodialysis. Also provided herein are methods of administering pharmaceutically acceptable sodium thiosulfate to a subject undergoing hemodialysis.

18 Claims, 1 Drawing Sheet

(56) References Cited

U.S. PATENT DOCUMENTS

| | | | |
|---|---|---|---|
| 2007/0154570 A1 | 7/2007 | Miller et al. | |
| 2007/0199898 A1 | 8/2007 | Sakai et al. | |
| 2009/0304600 A1 | 12/2009 | Shetty | |
| 2010/0247682 A1 | 9/2010 | Gladwin et al. | |
| 2012/0321724 A1 | 12/2012 | Bryan | |
| 2014/0350097 A1 | 11/2014 | Lai | |
| 2017/0252368 A1 | 9/2017 | Sherman et al. | |
| 2017/0312309 A1* | 11/2017 | Shetty | A61K 33/00 |
| 2018/0256639 A1* | 9/2018 | Sherman | A61M 1/1654 |

OTHER PUBLICATIONS

Bryan et al., "Acute effects of hemodialysis on nitrite and nitrate: potential cardiovascular implications in dialysis patients", Free Radical Biology Medicine, 58:46-51 (2013).

Inrig et al., "Effect of low versus high dialysate sodium concentration on blood pressure and endothelial-derived vasoregulators during hemodialysis: a randomized crossover study", American Journal Kidney of Diseases, 65(3):464-473 (2015).

Locatelli et al., "Optimizing haemodialysate composition", Clinical Kidney Journal, 8(5):580-589 (2015).

Sam et al., "Composition and clinical use of hemodialysates", Hemodialysis International, 10(1):15-28 (2006).

International Search Report and Written Opinion of corresponding PCT Application No. PCT/US2018/021069 dated May 30, 2018 (14 pages).

Association for the Advancement of Medical Instrumentation, 2009, "ANSI/AAMI/ISO 13959:2009 Water for hemodialysis and related therapies" (27 pages).

Ivankovich et al., 1983, "Sodium Thiosulfate Disposition in Humans: Relation to Sodium Nitroprusside Toxicity," Anesthesiology, 58(1): 11-17.

* cited by examiner

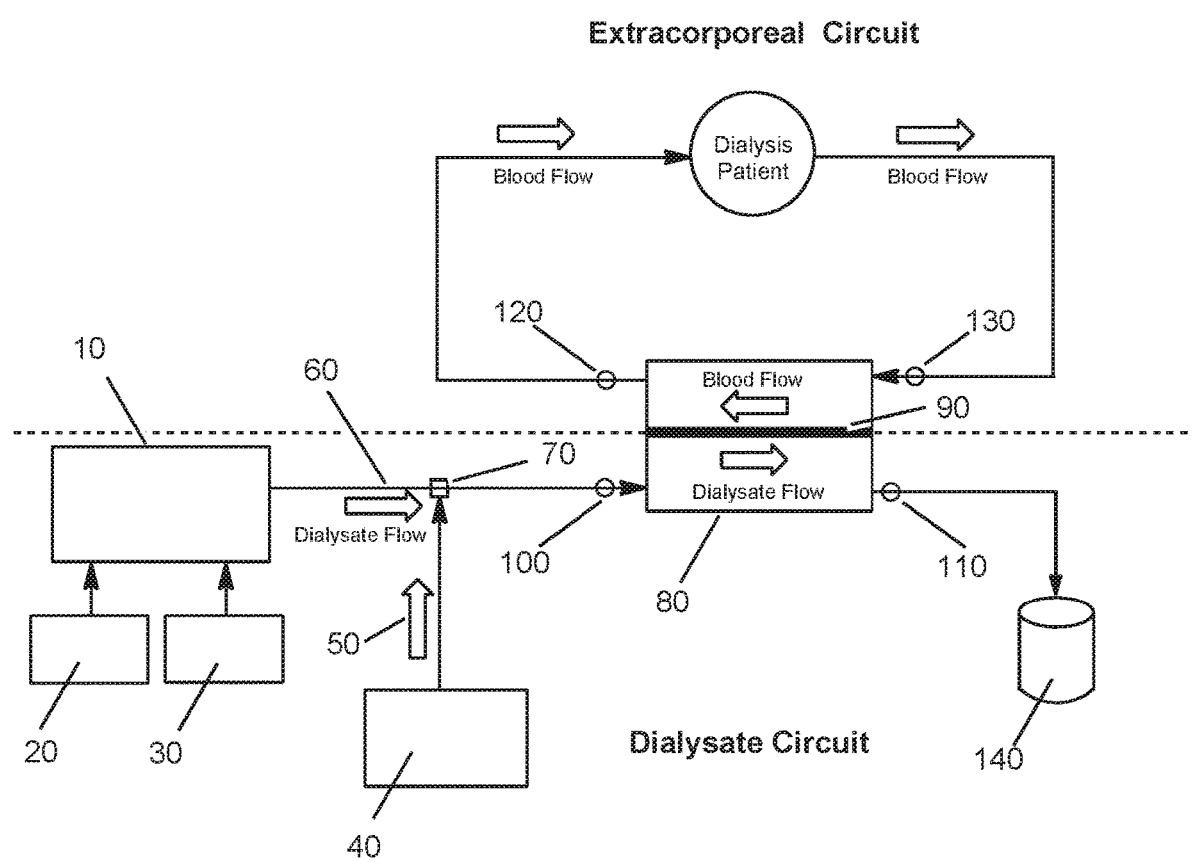

INTRADIALYTIC USE OF SODIUM THIOSULFATE

CROSS REFERENCE

This application claims the benefit of priority of U.S. Provisional Patent Application No. 62/468,871, filed Mar. 8, 2017, the content of which is incorporated herein by reference in its entirety.

FIELD

Provided herein are methods for maintaining physiological levels of thiosulfate in a subject undergoing hemodialysis. Also provided herein are methods of administering pharmaceutically acceptable sodium thiosulfate to a subject undergoing hemodialysis.

BACKGROUND

Patients with chronic kidney disease (CKD) experience deterioration of kidney function which results in a reduction in the excretion of metabolic waste products. The accumulation of metabolic waste products can become life threatening within days. Patients with little or no residual kidney function are characterized as having "end-stage renal disease." Therefore, such patients need an alternative means to excrete waste products to survive. Dialysis is a means to excrete waste products that involves the transfer of waste products from the blood to an external liquid that is subsequently discarded (*Am. J. Kidney Dis.* 2002, 39(Suppl. 1), S1-266).

Dialysis is defined as the movement of solutes and water between two liquids that are separated by a semipermeable "dialyzer membrane." In hemodialysis, blood flows across one side of the dialyzer membrane while a water-based solution called dialysate flows across the other side. Dialyzer membranes contain pores through which solutes can pass. The concentrations of solutes that are present in these two liquids equilibrate as osmotic forces push them out of the high concentration liquid, through the dialyzer membrane pores, and into the low concentration liquid.

Dialyzer membranes are designed with different pore sizes to limit the solutes that can pass through during hemodialysis. During hemodialysis, it may be harmful to remove from the blood an excessive amount of small molecule solutes, which can diffuse through dialyzer membrane.

Blood contains small molecular weight solutes such as thiosulfate ($S_2O_3^{2-}$). Thiosulfate anions have a molecular weight of approximately 112.13 Daltons. In the body, thiosulfate converts small amounts of cyanide ion into harmless products. Thiosulfate can also be metabolized to sulfate ($SO_4^{2-}$) (Gunnison et al., *Environ. Res.* 1981, 24, 432-443; Skarzynski et al., *Nature* 1959, 184, 994-995).

The Association for the Advancement of Medical Instrumentation (AAMI) established a quality specification limit for the sulfate content in water that is used in dialysis (maximum 100 mg per liter, i.e. 100 ppm) (# ANSI/AAMI/ISO 13959:2009). The AAMI also specified that the sulfate content in water should be measured using the "turbidimetric method". In this method, sulfate ion is precipitated in an acetic acid medium with barium chloride so as to form barium sulfate crystals of uniform size. Light absorbance of barium sulfate suspension is measured by a photometer and the sulfate anion concentration is determined by comparison of the reading with a standard curve (American Public Health Association. Available online at https://law.resource.org/pub/us/cfr/ibr/002/apha.method.4500-so42.1992.pdf). This test method does not distinguish between sulfate and thiosulfate. Instead, it is actually a measurement of both sulfate and thiosulfate. Therefore, the AAMI quality specification for sulfate is actually a limit of the sum of sulfate and thiosulfate in water that is used in dialysis.

Coronary bypass patients have decreased plasma thiosulfate levels (Ivankovich et al., *Anesthesiology* 1983, 58, 11-17). Coronary artery bypass surgery is often advised for patients with cardiovascular disease that is characterized by significant narrowings and blockages of the heart arteries caused by atherosclerosis. Atherosclerosis is a chronic inflammatory condition that begins with the formation of calcified plaque inside the vascular wall in large and mid-sized arteries. Calcium mineralization of the lumen in the atherosclerotic artery promotes and solidifies plaque formation causing narrowing of the vessel (Kalampogias et al. *Med. Chem.* 2016, 12, 103-113). Atherosclerotic plaques can cause significant narrowing in one or more coronary arteries. Myocardial infarction occurs when blood flow within a coronary artery is completely obstructed by an atherosclerotic plaque.

Cardiovascular disease accounts for more than half of all deaths of patients who require chronic hemodialysis (Go et al., *N. Eng. J. Med.* 2004, 351, 1296-1305).

There was a 1.7 fold increased risk of sudden death events in the 12 hour period beginning with the dialysis treatment. Sudden death events were increased both during the dialysis procedure itself and after treatment (Bleyer et al., *Kidney Int.* 2006, 12, 2268-2273).

Coincidentally, the concentration of thiosulfate in the plasma declines by over 60% during the first hour of hemodialysis and remains significantly depressed during the subsequent hours of a four-hour hemodialysis session. (Freise et al., *Free Radic. Biol. Med.* 2013, 58, 46-51)

Sodium thiosulfate can be administered into the blood by intravenous injection; however, it would be ineffective in maintaining physiological levels with dialysis patients since it is rapidly removed during hemodialysis. At this time, there is no effective method for maintaining physiological levels of thiosulfate in the blood of patients who undergo hemodialysis. There is also no satisfactory method for administrating sodium thiosulfate to patients during hemodialysis.

SUMMARY

The present disclosure provides methods for maintaining physiological levels of thiosulfate in a subject undergoing hemodialysis. The present disclosure also provides methods for preventing atherosclerosis, myocardial infarction, sudden cardiac death, stroke, cardiovascular disease, high blood pressure, pulmonary hypertension, and/or renal hypertension in a subject undergoing hemodialysis. The present disclosure also provides methods for administering sodium thiosulfate in a subject undergoing hemodialysis.

In some embodiments, provided herein are methods for maintaining physiological levels of thiosulfate in a subject undergoing hemodialysis, comprising intradialytically contacting said subject's blood with a dialyzer membrane that is also in contact with a thiosulfate-spiked dialysate, wherein an aqueous solution comprising sodium thiosulfate is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0.

In some embodiments, also provided herein are methods for maintaining physiological levels of thiosulfate in a subject undergoing hemodialysis, comprising intradialytically contacting said subject's blood with a thiosulfate-spiked dialysate, wherein an aqueous solution comprising sodium thiosulfate is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0.

In some embodiments, also provided herein are methods for preventing atherosclerosis in a subject undergoing dialysis, comprising intradialytically contacting said subject's blood with a dialyzer membrane that is also in contact with a thiosulfate-spiked dialysate, wherein an aqueous solution comprising sodium thiosulfate is added to said unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0.

In some embodiments, also provided herein are methods for preventing myocardial infarction in a subject undergoing dialysis, comprising intradialytically contacting said subject's blood with a dialyzer membrane that is also in contact with a thiosulfate-spiked dialysate, wherein an aqueous solution comprising sodium thiosulfate is added to said unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0.

In some embodiments, also provided herein are methods for preventing sudden cardiac death in a subject undergoing dialysis, comprising intradialytically contacting said subject's blood with a dialyzer membrane that is also in contact with a thiosulfate-spiked dialysate, wherein an aqueous solution comprising sodium thiosulfate is added to said unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0.

In some embodiments, also provided herein are methods for preventing stroke in a subject undergoing dialysis, comprising intradialytically contacting said subject's blood with a dialyzer membrane that is also in contact with a thiosulfate-spiked dialysate, wherein an aqueous solution comprising sodium thiosulfate is added to said unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0.

In some embodiments, also provided herein are methods for preventing cardiovascular disease that is characterized by tissue ischemia including angina, cerebral vasospasm, claudication, critical limb ischemia, peripheral vascular disease, and sickle cell crisis in a subject undergoing dialysis, comprising intradialytically contacting said subject's blood with a dialyzer membrane that is also in contact with a thiosulfate-spiked dialysate, wherein an aqueous solution comprising sodium thiosulfate is added to said unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0.

In some embodiments, also provided herein are methods for preventing high blood pressure, pulmonary hypertension, and renal hypertension in a subject undergoing dialysis, comprising intradialytically contacting said subject's blood with a dialyzer membrane that is also in contact with a thiosulfate-spiked dialysate, wherein an aqueous solution comprising sodium thiosulfate is added to said unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0.

In some embodiments, also provided herein are methods for administering sodium thiosulfate to a subject undergoing dialysis, comprising intradialytically contacting said subject's blood with a dialyzer membrane that is also in contact with a thiosulfate-spiked dialysate, wherein an aqueous solution comprising sodium thiosulfate is added to said unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0.

BRIEF DESCRIPTION OF THE DRAWINGS

FIG. 1. is a schematic diagram of elements of the flow path of the dialysate, the blood of patients, and the aqueous solution comprising sodium thiosulfate. (10) Dialysis machine; (20) acid concentrate solution; (30) bicarbonate concentrate solution; (40) aqueous solution comprising sodium thiosulfate; (50) flow of aqueous solution comprising sodium thiosulfate; (60) dialysate tubing; (70) valve; (80) dialyzer; (90) dialyzer membrane; (100) detection point "pre" dialyzer membrane; (110) detection point "post" dialyzer membrane; (120) detection point "V"; (130) detection point "A"; (140) used dialysate.

DETAILED DESCRIPTION

The following detailed description is not to be taken in a limiting sense, but is made merely for the purpose of illustrating the embodiments provided herein.

To facilitate understanding of the disclosure set forth herein, a number of terms are defined below.

Generally, the nomenclature used herein and the laboratory procedures in inorganic chemistry, analytical chemistry, organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject. In one embodiment, the subject has or is at risk for a disease, disorder or condition provided herein. In another embodiment, the subject has or is at risk for a disease, disorder or condition wherein the disease, disorder or condition, or a symptom thereof, can be treated, prevented or ameliorated by the administration of sodium thiosulfate. In another embodiment, the subject is an end stage renal disease (ESRD) patient who is placed on regular hemodialysis. In another embodiment, the subject is a patient with some or no renal function who undergoes dialysis to reduce wastes from the blood to safe levels. In another embodiment, the steady-state plasma concentration of thiosulfate in the subject undergoing hemodialysis is significantly reduced as a result of about 3 to about 5 hours of hemodialysis. In another embodiment, the subject has plasma levels of thiosulfate that are below normal physiological levels.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptom(s); barring a subject from acquiring a disease; or reducing a subject's risk of acquiring a disorder, disease, or condition.

In general, conventional dialysates are defined as any formulation heretofore known, whether or not proprietary, including those that are recently patented. Many of these are specially formulated to satisfy the needs of a particular type. For example, U.S. Pat. No. 6,436,969 discloses compositions containing AGE inhibitors, U.S. Pat. No. 5,869,444 claims solutions contain an osmotically effective mixture of peptides, U.S. Pat. Nos. 6,306,836 and 6,380,163 disclose peritoneal dialysis solution utilizing amino acids to achieve osmotic balance.

The term "bicarbonate concentrate solution" refers to aqueous solution comprising a bicarbonate salt or a mixture of bicarbonate salts and water that meets or exceeds the current hemodialysis water quality standards as listed in ANSI/AAMI/ISO #13959:2009 (hereafter called "purified water"). Minntech Renal Systems in Minneapolis, Minn. supplies Centrisol® Bicarbonate Concentrate Powder MB-330. Each bag of Centrisol® Bicarbonate Concentrate Powder 45X MB-330 contains about 650 grams of sodium bicarbonate. The contents of a bag are mixed with purified water to make about 8 liters of dialysate bicarbonate concentrate solution.

The term "acid concentrate solution" refers to aqueous solution comprising acid or a mixture of acids and purified water. Representative examples of acid include, but are not limited to hydrochloric acid, acetic acid, citric acid, and peracetic acid. Minntech Renal Systems in Minneapolis, Minn. supplies Centrisol® Acid Concentrate 45X SB-111. Each bag of Centrisol® Acid Concentrate Powder 45X contains acetate, bicarbonate, calcium, chloride, dextrose, magnesium, and potassium. One volume part of acid concentrate should be mixed with 1.72 volume parts of properly mixed MB-330 Series Sodium Bicarbonate Concentrate and 42.28 volume parts of purified water to prepare 45 volume parts of dialysate solution.

The term "dialysis machine" is a machine comprising an extracorporeal circuit and a dialysate circuit. The extracorporeal circuit further comprises tubing, blood pump, heparin pump, kidney, and monitors for blood flow, blood pressure, and air bubbles. The dialysate circuit further comprises dialysate tubing, dialysate pump, and monitors for dialysate flow, dialysate pressure, and air bubbles. Presently, dialysis machines utilize an automated proportioning system to mix the acid concentrate solution, bicarbonate concentrate solution and purified water in specific proportions to general the dialysate. The dialysate concentrate solutions (acid and bicarbonate) are usually supplied by the manufacturer either as a premixed powder (as bicarbonate powder) that is added to purified water in large reservoirs or as a solution (as acid concentrate) ready to use. The dialysate concentrate solutions are pumped into a chamber in the dialysis machine where they are mixed with purified water to make the dialysate.

The term "dialysate tubing" refers to the tubing connects a dialysis machine and a dialyzer.

The term "dialyzer" is meant to include an artificial kidney comprising a synthetic or semi-synthetic semipermeable membrane (hereafter called "dialyzer membrane") made of chemical materials including but not limited to cellulose acetate, cupraphane, polyacrilonitrile, polymethyl methacrylate, or polysulfone. A constant flow of blood on one side the membrane and dialysate on the other allows removal of wastes in the blood. An artificial kidney can be used to perform hemodialysis, during which diffusion is the major mechanism for solute removal. On the other hand hemofiltration (also called hemodiafiltration and diafiltration) relies on ultrafiltration and convective transport rather than diffusion to move solutes across a high porosity semipermeable membrane.

The term "unspiked dialysate" refers to the dialysate solution mixed by the dialysis machine and pumped into the dialysate tubing to flow to the dialyzer membrane before the aqueous solution comprising sodium thiosulfate is added to the dialysate tubing through a valve.

The term "thiosulfate-spiked dialysate" refers to dialysate solution in the dialysate tubing after the aqueous solution comprising sodium thiosulfate is added to the dialysate tubing through a valve.

The term "therapeutically effective amount" is meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a cell, tissue, system, animal, or human, which is being sought by a researcher, veterinarian, medical doctor, or clinician. In one embodiment, a therapeutically effective amount is an amount sufficient to maintain a subject's blood level of thiosulfate at about physiological levels.

The term "about" or "approximately" means an acceptable error for a particular value as determined by one of ordinary skill in the art, which depends in part on how the value is measured or determined. In some embodiments, the term "about" or "approximately" means within 1, 2, 3, or 4 standard deviations. In some embodiments, the term "about" or "approximately" means within 15%, 10%, 9%, 8%, 7%, 6%, 5%, 4%, 3%, 2%, 1%, 0.5%, or 0.05% of a given value or range. In some embodiments, it is contemplated that the values preceded by the term "about" or "approximately" are exact.

The term "normal physiological levels" of thiosulfate means the levels of thiosulfate that occur in a healthy adult subject. In one embodiment, the normal physiological level of thiosulfate in a subject is between 1 and 10 micromolar.

In some embodiments, the methods provided herein comprise the use of purified forms of sodium thiosulfate, such as sodium thiosulfate pentahydrate ($Na_2S_2O_3.5H_2O$). In one embodiment, provided herein is pharmaceutical grade sodium thiosulfate. In another embodiment, provided herein are forms of sodium thiosulfate meeting or exceeding one, more than one or all FDA standards for sodium thiosulfate for pharmaceutical use. In another embodiment, provided herein are forms of sodium thiosulfate that were manufactured according to Good Manufacturing Practices (GMP) as detailed in the United States Code of Federal Regulations 21 CFR 211. In one embodiment, the pharmaceutically acceptable sodium thiosulfate is that disclosed in U.S. Pat. Pub. No. 2011/0008467, filed Jul. 7, 2010, which is incorporated by reference herein in its entirety.

In one embodiment, the sodium thiosulfate is solid.

In one embodiment, the appearance of the sodium thiosulfate is colorless crystals.

In one embodiment, the appearance of a 10% solution containing the sodium thiosulfate is clear and colorless.

In one embodiment, the sodium thiosulfate is odorless.

In one embodiment, the presence of sodium thiosulfate in a 10% solution containing sodium thiosulfate provided herein is identified by the discharge of yellow color after the addition of a few drops of iodine TS.

In one embodiment, the presence of sodium in sodium thiosulfate provided herein is confirmed according to Method 191 in USP XXXII (2009), which is incorporated by reference herein in its entirety.

In one embodiment, the presence of thiosulfate in sodium thiosulfate provided herein is confirmed according to Method 191 in USP XXXII (2009).

In one embodiment, the sodium thiosulfate pentahydrate provided herein contains no less than about 99% by weight and/or no greater than about 100.5% by weight of sodium thiosulfate calculated on the anhydrous basis. In some embodiments, the amount of anhydrous sodium thiosulfate in the sodium thiosulfate pentahydrate provided herein is determined according to USP colorimetric assay (USP XXXII (2009)).

In one embodiment, the sodium thiosulfate pentahydrate provided herein contains no less than about 98% by weight and no greater than about 102% by weight of sodium thiosulfate on an anhydrous basis as measured by ion chromatography.

In one embodiment, the sodium thiosulfate pentahydrate provided herein contains no less than about 98% by weight and/or no greater than about 102% by weight of sodium thiosulfate calculated on the anhydrous basis. In some embodiments, the amount of sodium thiosulfate anhydrous in the sodium thiosulfate pentahydrate provided herein is determined by an ion chromatography. In some embodiments, the amount of anhydrous sodium thiosulfate in the sodium thiosulfate pentahydrate provided herein is determined by an ion chromatography with electrochemical conductivity detection as described herein.

In another embodiment, the sodium thiosulfate provided herein has a pH between about 6 to about 8 when measured in a 10% solution at 25° C. In some embodiments, the pH of the sodium thiosulfate provided herein is measured using a pH meter. In some embodiments, the pH of the sodium thiosulfate provided herein is determined according to Method 791 in USP XXXII (2009).

In yet another embodiment, the sodium thiosulfate provided herein has water content of about 32% to about 37% by weight. In some embodiments, the water content in the sodium thiosulfate provided herein is determined by Karl Fischer method. In some embodiments, the water content in the sodium thiosulfate provided herein is quantitated according to Method 921 in USP XXXII (2009).

In yet another embodiment, the heavy metal content in the sodium thiosulfate provided herein is no greater than about 10 ppm of a heavy metal. The heavy metal content in the sodium thiosulfate provided herein is determined according to Method 231 in USP XXXII (2009).

In yet another embodiment, the sodium thiosulfate provided herein contains no greater than about 0.02% by weight of carbonate. In yet another embodiment, the sodium thiosulfate provided herein contains no greater than about 0.01% by weight of carbonate. In some embodiments, the amount of carbonate in the sodium thiosulfate provided herein is determined by contacting a sodium thiosulfate sample with an acid, such as phosphoric acid, to convert carbonate to carbon dioxide and determining the amount of the carbon dioxide using a non-dispersive infrared detector.

In yet another embodiment, the sodium thiosulfate provided herein contains no greater than about 0.005% by weight of insoluble matter. In some embodiments, the amount of insoluble material in the sodium thiosulfate provided herein is determined by dissolving 10 grams of the sodium thiosulfate provided herein in 100 mL of water, the solution is heated to boiling for 1 hr, the solution is filtered, washed with hot water, dried, cooled in a desiccator, and weighed.

In yet another embodiment, the sodium thiosulfate provided herein contains no greater than about 200 ppm by weight of chloride. In some embodiments, the chloride content in the sodium thiosulfate provided herein is determined according to Method 221 in USP XXXII (2009).

In yet another embodiment, the sodium thiosulfate provided herein contains no greater than about 0.002% by weight of iron. In some embodiments, the iron content in the sodium thiosulfate provided herein is determined using inductively coupled plasma mass spectrometry (ICP-MS). In some embodiments, the iron content in the sodium thiosulfate provided herein is determined using inductively coupled plasma-optical emission spectroscopy (ICP-OES). In some embodiments, the iron content in the sodium thiosulfate provided herein is determined according to Method 241 in USP XXXII (2009).

In yet another embodiment, the sodium thiosulfate provided herein contains no greater than about 0.001% by weight of lead. In some embodiments, the lead content in the sodium thiosulfate provided herein is determined according to Method 251 in USP XXXII (2009).

In yet another embodiment, the sodium thiosulfate provided herein contains no greater than about 0.01% by weight of calcium. In some embodiments, the calcium content in the sodium thiosulfate provided herein is determined using ICP-MS. In some embodiments, the calcium content in the sodium thiosulfate provided herein is determined using flame emission spectrometry (FES).

In yet another embodiment, the sodium thiosulfate provided herein causes no turbidity when ammonium oxalate test solution prepared according to USP XXXII (2009) is added to an aqueous solution containing sodium thiosulfate (e.g., one gram of sodium thiosulfate dissolved in 20 mL of water).

In yet another embodiment, the sodium thiosulfate provided herein contains no greater than about 0.005% by weight of potassium. In some embodiments, the potassium content in the sodium thiosulfate provided herein is determined using ICP-MS. In some embodiments, the potassium content in the sodium thiosulfate provided herein is determined using FES.

In yet another embodiment, the sodium thiosulfate provided herein contains no greater than about 0.05% by weight of sulfite, or no greater than about 0.1% by weight of sulfite. In some embodiments, the sulfite content in the sodium thiosulfate provided herein is determined according to the method for the determination of sulfite in American Chemical Society, Reagent Chemicals, $10^{th}$ Edition, incorporated by reference herein in its entirety.

In yet another embodiment, the sodium thiosulfate provided herein contains no greater than about 0.05%, no greater than about 0.1%, no greater than about 0.25%, or no greater than about 0.5% by weight of sulfate (as $SO_4^{2-}$). In some embodiments, the sulfate content in the sodium thiosulfate provided herein is determined according to the method for the determination of sulfate in American Chemical Society, Reagent Chemicals, $10^{th}$ Edition.

In yet another embodiment, the sodium thiosulfate provided herein contains no greater than about 0.001% by weight of sulfide. In some embodiments, the sulfide content in the sodium thiosulfate provided herein is determined by the addition of lead (II) nitrate using methods described herein.

In yet another embodiment, the sodium thiosulfate provided herein contains no greater than about 0.002% by weight of nitrogen compounds (as N). In some embodiments, the nitrogen compounds (as N) content in the sodium thiosulfate provided herein is determined according to the method for the determination of nitrogen compounds in American Chemical Society, Reagent Chemicals, $10^{th}$ Edition.

In yet another embodiment, the sodium thiosulfate provided herein contains no greater than about 10 ppm, no greater than about 100 ppm, no greater than about 500 ppm, no greater than about 1000 ppm, or no greater than about 5000 ppm of total volatile organic carbon. In some embodiments, the sodium thiosulfate provided herein contains no greater than the specific limits set forth in ICH Q3C(R3) for organic volatile impurities or a particular solvent (e.g., ethanol), the disclosure of which is incorporated by references in its entirety. In some embodiments, the content of organic volatile impurities is determined according to Method 467 in USP XXXII (2009).

In yet another embodiment, the sodium thiosulfate provided herein contains total NPOC of no greater than about 60 ppb, no greater than about 2.5 ppm, no greater than about 8 ppm, no greater than about 10 ppm, no greater than about 20 ppm, no greater than about 25 ppm, or no greater than about 50 ppm. In some embodiments, the sodium thiosulfate provided herein contains total NPOC of no greater than about 12 ppm. In some embodiments, the total NPOC in the sodium thiosulfate provided herein is determined using methods described herein. In some embodiments, the total NPOC in the sodium thiosulfate provided herein is determined by a) contacting the sodium thiosulfate with a predetermined amount of an inorganic acid-containing aqueous solution to form an aqueous sample solution; b) removing precipitates from the aqueous sample solution; c) contacting the sample solution with a predetermined amount of an oxidizer; and d) converting the organic carbon in the sample solution into carbon dioxide under a supercritical water oxidation (SCWO) condition.

In yet another embodiment, the sodium thiosulfate provided herein contains no greater than about 0.05 ppm of mercury. In some embodiments, the mercury content in the sodium thiosulfate provided herein is determined using ICP-MS. In some embodiments, the mercury content in the sodium thiosulfate provided herein is determined using ICP-OES. In some embodiments, the mercury content in the sodium thiosulfate provided herein is determined according to Method 261 in USP XXXII (2009).

In yet another embodiment, the sodium thiosulfate provided herein contains no greater than about 2 ppm of aluminum. In some embodiments, the aluminum content in the sodium thiosulfate provided herein is determined using ICP-MS. In some embodiments, the aluminum content in the sodium thiosulfate provided herein is determined using ICP-OES. In some embodiments, the aluminum content in the sodium thiosulfate provided herein is determined according to Method 206 in USP XXXII (2009).

In yet another embodiment, the sodium thiosulfate provided herein contains no greater than about 3 ppm of arsenic. In some embodiments, the arsenic content in the sodium thiosulfate provided herein is determined using ICP-MS. In some embodiments, the arsenic content in the sodium thiosulfate provided herein is determined using ICP-OES. In some embodiments, the arsenic content in the sodium thiosulfate provided herein is determined according to Method 211 in USP XXXII (2009).

In yet another embodiment, the sodium thiosulfate provided herein contains no greater than about 0.003% by weight of selenium. In some embodiments, the selenium content in the sodium thiosulfate provided herein is determined using ICP-MS. In some embodiments, the selenium content in the sodium thiosulfate provided herein is determined using ICP-OES. In some embodiments, the selenium content in the sodium thiosulfate provided herein is determined according to Method 291 in USP XXXII (2009).

In yet another embodiment, the total aerobic count of microbial load in the sodium thiosulfate provided herein is no greater than about 100 Colony Forming Units per gram (CFU/g). The total aerobic count of microbial load in the sodium thiosulfate provided herein is quantitated according to Method 61 in USP XXXII (2009).

In yet another embodiment, the total yeast and mold count in the sodium thiosulfate provided herein is no greater than about 20 CFU/g. The total yeast and mold count in the sodium thiosulfate provided herein is quantitated according to Method 61 in USP XXXII (2009).

In yet another embodiment, the sodium thiosulfate provided herein contains no greater than about 0.02 Endotoxin Units per milligram (EU/mg), no greater than about 0.1 EU/mg, or no greater than about 0.25 EU/mg of bacterial endotoxins. The amount of bacterial endotoxins in the sodium thiosulfate provided herein is quantitated according to Method 85 in USP XXXII (2009).

In yet another embodiment, the sodium thiosulfate provided herein contains no greater than about 0.01% of a residual anti-caking agent.

In yet another embodiment, the sodium thiosulfate provided herein is characterized by one or more of the following:

containing no less than about 99% by weight and/or no greater than about 100.5% by weight of sodium thiosulfate on an anhydrous basis determined according to USP colormimetric assay;

containing no less than about 98% by weight and/or no greater than about 102% by weight of sodium thiosulfate on an anhydrous basis determined according to ion chromatography assay;

having a pH between about 6 to about 8 when measured in a 10% solution at 25° C.;

having water content of about 32% to about 37% by weight;

having an appearance of colorless crystals;

having a clear and colorless appearance as a 10% solution;

having no odor;

having a positive identification test for sodium;

having a positive identification test for thiosulfate;

having no turbidy when mixed with ammonium oxalate TS;

having heavy metal content of no greater than about 10 ppm;

containing no greater than about 0.01% by weight of carbonate;

containing no greater than about 0.005% by weight of insoluble matter;

containing no greater than about 200 ppm of chloride;

containing no greater than about 0.001% by weight of sulfide;

containing no greater than about 0.05% or no greater than about 0.1% by weight of sulfite;

containing no greater than about 0.05%, no greater than about 0.1%, no greater than about 0.25%, or no greater than about 0.5% by weight of sulfate;

containing no greater than about 0.002% by weight of iron;

containing no greater than about 0.01% by weight of calcium;

containing no greater than about 0.005% by weight of potassium;

containing no greater than about 10 ppm, no greater than about 100 ppm, no greater than about 500 ppm, no greater than about 1000 ppm, or no greater than 5000 ppm of organic volatile impurities;

having total NPOC of no greater than 60 ppb, no greater than about 2.5 ppm, no greater than about 8 ppm, no greater than about 10 ppm, no greater than about 20 ppm, no greater than about 25 ppm, or no greater than about 50 ppm;

containing no greater than about 0.05 ppm of mercury;

containing no greater than about 2 ppm of aluminum;

containing no greater than about 3 ppm of arsenic;

containing no greater than 0.001% by weight of lead;

containing no greater than about 0.002% by weight of nitrogen compounds (as N);

containing no greater than about 0.003% by weight of selenium;

containing no greater than 0.01% of a residual anti-caking agent;

having a total aerobic count of microbial load of no greater than about 100 CFU/g;

having a total yeast and mold count of no greater than about 20 CFU/g; and containing no greater than about 0.02 EU/mg, no greater than 0.1 EU/mg, or no greater than about 0.25 EU/mg of bacterial endotoxins.

In still another embodiment, the sodium thiosulfate provided herein is characterized by one or more of the following:

containing no less than about 99% by weight and/or no greater than about 100.5% by weight of sodium thiosulfate on an anhydrous basis determined according to USP colormimetric assay;

containing no less than about 98% by weight and/or no greater than about 102% by weight of sodium thiosulfate on an anhydrous basis determined according to ion chromatography assay;

having a pH between about 6 to about 8 when measured in a 10% solution at 25° C.;

having water content of about 32% to about 37% by weight;

having an appearance of colorless crystals;

having a clear and colorless appearance as a 10% solution;

having no odor;

having a positive identification test for sodium;

having a positive identification test for thiosulfate;

having no turbidy when mixed with ammonium oxalate TS;

having heavy metal content of no greater than about 10 ppm;

containing no greater than about 0.01% by weight of carbonate;

containing no greater than about 0.005% by weight of insoluble matter;

containing no greater than about 200 ppm of chloride;

containing no greater than about 0.001% by weight of sulfide;

containing no greater than about 0.05% or no greater than about 0.1% by weight of sulfite;

containing no greater than about 0.05%, no greater than about 0.1%, no greater than about 0.25%, or no greater than about 0.5% by weight of sulfate;

containing no greater than about 0.002% by weight of iron;

containing no greater than about 0.01% by weight of calcium;

containing no greater than about 0.005% by weight of potassium;

containing no greater than about 10 ppm, no greater than about 100 ppm, no greater than about 500 ppm, no greater than about 1000 ppm, or no greater than 5000 ppm of organic volatile impurities;

having total NPOC of no greater than 60 ppb, no greater than about 2.5 ppm, no greater than about 8 ppm, no greater than about 10 ppm, no greater than about 20 ppm, no greater than about 25 ppm, or no greater than about 50 ppm;

containing no greater than about 0.05 ppm of mercury;

containing no greater than about 2 ppm of aluminum;

containing no greater than about 3 ppm of arsenic;

containing no greater than 0.001% by weight of lead;

containing no greater than about 0.002% by weight of nitrogen compounds (as N);

containing no greater than about 0.003% by weight of selenium;

having a total aerobic count of microbial load of no greater than about 100 CFU/g;

having a total yeast and mold count of no greater than about 20 CFU/g; and containing no greater than about 0.02 EU/mg, no greater than 0.1 EU/mg, or no greater than about 0.25 EU/mg of bacterial endotoxins.

In some embodiments, where the sodium thiosulfate is described as "containing no greater than" a certain amount of a particular material, the sodium thiosulfate does not contain a detectable amount of the material.

Methods of Maintaining Physiological Level of Thiosulfate

Provided herein are methods for maintaining physiological levels of thiosulfate in a subject undergoing hemodialysis, comprising intradialytically contacting said subject's blood with a dialyzer membrane that is also in contact with a thiosulfate-spiked dialysate, wherein an aqueous solution comprising sodium thiosulfate is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0.

Also provided herein are methods for maintaining physiological levels of thiosulfate in a subject undergoing hemodialysis, comprising intradialytically contacting said subject's blood with a thiosulfate-spiked dialysate, wherein an aqueous solution comprising sodium thiosulfate is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0.

In one embodiment, the subject is a mammal. In another embodiment, the subject is a human.

In one embodiment, the physiological level of thiosulfate in said subject is no more than about 100 micromolar. In another embodiment, the physiological level of thiosulfate in said subject is no more than about 10 micromolar. In yet another embodiment, the physiological level of thiosulfate in said subject is between about 500 nanomolar and about 10 micromolar. In yet another embodiment, the physiological level of thiosulfate in said subject is between about 1 micromolar and about 5 micromolar. In yet another embodiment, the physiological level of thiosulfate in said subject is about 3 micromolar.

In one embodiment, the concentration of thiosulfate in said thiosulfate-spiked dialysate is no more than 100 micromolar. In another embodiment, the concentration of thiosulfate in said thiosulfate-spiked dialysate is no more than about 10 micromolar. In yet another embodiment, the concentration of thiosulfate in said thiosulfate-spiked dialysate is between about 500 nanomolar and about 10 micromolar. In yet another embodiment, the concentration of thiosulfate in said thiosulfate-spiked dialysate is between about 1 micromolar and about 5 micromolar. In yet another embodiment, the concentration of thiosulfate in said thiosulfate-spiked dialysate is about 3 micromolar.

In some embodiments, the aqueous solution comprising sodium thiosulfate comprises no more than about 10 mg/L, about 50 mg/L, about 100 mg/L, about 150 mg/L, about 200 mg/L, about 250 mg/L, about 300 mg/L, about 350 mg/L, about 400 mg/L, about 450 mg/mL, or about 500 mg/L of sodium thiosulfate.

In some embodiments, the water comprises no more than about 10 mg/L, about 50 mg/L, about 100 mg/L, about 150 mg/L, about 200 mg/L, about 250 mg/L, about 300 mg/L, about 350 mg/L, about 400 mg/L, about 450 mg/mL, or about 500 mg/L of thiosulfate.

In one embodiment, the aqueous solution comprising sodium thiosulfate is added to said unspiked dialysate through a valve that is attached to dialysate tubing at a location before said tubing connects to the dialyzer. In another embodiment, said unspiked dialysate flows through said dialysis tubing at a rate between about 200 mL/min and about 1000 mL/min. In yet another embodiment, said unspiked dialysate flows through said dialysis tubing at a rate between about 300 mL/min and about 900 mL/min. In yet another embodiment, said unspiked dialysate flows through said dialysis tubing at a rate between about 400 mL/min and about 800 mL/min. In yet another embodiment, said unspiked dialysate flows through said dialysis tubing at a rate between about 500 mL/min and about 700 mL/min. In yet another embodiment, said unspiked dialysate flows through said dialysis tubing at a rate about 600 mL/min.

In one embodiment, the aqueous solution comprising sodium thiosulfate is added through the valve to the unspiked dialysate at a rate between about 0 mL/hr and about 750 mL/hr, at a rate between about 50 mL/hr and about 650 mL/hr, at a rate between about 100 mL/hr and about 550 mL/hr, at a rate between about 150 mL/hr and about 450 mL/hr, or at a rate between about 200 mL/hr and about 350 mL/hr. In another embodiment, the aqueous solution comprising sodium thiosulfate is added through the valve to the unspiked dialysate at a rate about 250 mL/hr.

In yet another embodiment, the pH of said thiosulfate-spiked dialysate is between about 7.0 and about 8.0. In yet another embodiment, the pH of said thiosulphate-spiked dialysate is between about 7.1 and about 8.0. In yet another embodiment, the pH of said thiosulfate-spiked dialysate is between about 7.3 and about 8.0. In yet another embodiment, the pH of said sodium thiosulfate-spiked dialysate is between about 7.3 and about 7.5. In yet another embodiment, the pH of said sodium thiosulfate-spiked dialysate is about 7.4.

In yet another embodiment, said subject is a human with chronic renal failure. In another embodiment, the said subject is a human with acute renal failure.

In yet another embodiment, said subject undergoes hemodialysis from one to ten times per week. In yet another embodiment, the said subject undergoes hemodialysis from three to seven times per week.

In certain embodiments, the methods provided herein return and/or maintain the subject's plasma levels of thiosulfate to normal physiological levels.

Methods of Prevention

1. Methods of Preventing Atherosclerosis

In some embodiments, provided herein are methods for preventing atherosclerosis in a subject undergoing dialysis, comprising intradialytically contacting said subject's blood with a dialyzer membrane that is also in contact with a thiosulfate-spiked dialysate, wherein an aqueous solution comprising sodium thiosulfate is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0.

In some embodiments, further provided herein are methods for preventing atherosclerosis in a subject undergoing hemodialysis, comprising intradialytically contacting said subject's blood with a thiosulfate-spiked dialysate, wherein an aqueous solution comprising sodium thiosulfate is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0.

In one embodiment, the subject is a mammal. In another embodiment, the subject is a human.

In certain embodiments, the methods provided herein return and/or maintain the subject's plasma levels of thiosulfate to normal physiological levels.

2. Methods of Preventing Myocardial Infarction

In some embodiments, provided herein are methods for preventing myocardial infarction in a subject undergoing dialysis, comprising intradialytically contacting said subject's blood with a dialyzer membrane that is also in contact with a thiosulfate-spiked dialysate, wherein an aqueous solution comprising sodium thiosulfate is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0.

In some embodiments, further provided herein are methods for preventing myocardial infarction in a subject undergoing hemodialysis, comprising intradialytically contacting said subject's blood with a thiosulfate-spiked dialysate, wherein an aqueous solution comprising sodium thiosulfate is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0.

In one embodiment, the subject is a mammal. In another embodiment, the subject is a human.

In certain embodiments, the methods provided herein return and/or maintain the subject's plasma levels of thiosulfate to normal physiological levels.

3. Methods of Preventing Sudden Cardiac Death

In some embodiments, provided herein are methods for preventing sudden cardiac death in a subject undergoing dialysis, comprising intradialytically contacting said subject's blood with a dialyzer membrane that is also in contact with a thiosulfate-spiked dialysate, wherein an aqueous solution comprising sodium thiosulfate is added to said unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0.

In some embodiments, further provided herein are methods for preventing sudden cardiac death in a subject undergoing hemodialysis, comprising intradialytically contacting said subject's blood with a thiosulfate-spiked dialysate, wherein an aqueous solution comprising sodium thiosulfate is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0.

In one embodiment, the subject is a mammal. In another embodiment, the subject is a human.

In certain embodiments, the methods provided herein return and/or maintain the subject's plasma levels of thiosulfate to normal physiological levels.

4. Methods of Preventing Stroke

In some embodiments, provided herein are methods for preventing stroke in a subject undergoing dialysis, comprising intradialytically contacting said subject's blood with a dialyzer membrane that is also in contact with a thiosulfate-spiked dialysate, wherein an aqueous solution comprising sodium thiosulfate is added to said unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0.

In some embodiments, further provided herein are methods for preventing stroke in a subject undergoing hemodialysis, comprising intradialytically contacting said subject's blood with a thiosulfate-spiked dialysate, wherein an aqueous solution comprising sodium thiosulfate is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0.

In one embodiment, the subject is a mammal. In another embodiment, the subject is a human.

In certain embodiments, the methods provided herein return and/or maintain the subject's plasma levels of thiosulfate to normal physiological levels.

5. Methods of Preventing Cardiovascular Disease

In some embodiments, provided herein are methods for preventing cardiovascular disease that is characterized by tissue ischemia including angina, cerebral vasospasm, claudication, critical limb ischemia, peripheral vascular disease, and sickle cell crisis in a subject undergoing dialysis, comprising intradialytically contacting said subject's blood with a dialyzer membrane that is also in contact with a thiosulfate-spiked dialysate, wherein an aqueous solution comprising sodium thiosulfate is added to said unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0.

In some embodiments, further provided herein are methods for preventing cardiovascular disease that is characterized by tissue ischemia including angina, cerebral vasospasm, claudication, critical limb ischemia, peripheral vascular disease, and sickle cell crisis in a subject undergoing dialysis, comprising intradialytically contacting said subject's blood with a thiosulfate-spiked dialysate, wherein an aqueous solution comprising sodium thiosulfate is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0.

In one embodiment, the subject is a mammal. In another embodiment, the subject is a human.

In certain embodiments, the methods provided herein return and/or maintain the subject's plasma levels of thiosulfate to normal physiological levels.

6. Methods of Preventing High Blood Pressure, Pulmonary Hypertension, and Renal Hypertension In some embodiments, provided herein are methods for preventing high blood pressure, pulmonary hypertension, and renal hypertension in a subject undergoing dialysis, comprising intradialytically contacting said subject's blood with a dialyzer membrane that is also in contact with a thiosulfate-spiked dialysate, wherein an aqueous solution comprising sodium thiosulfate is added to said unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0.

In some embodiments, further provided herein are methods for preventing high blood pressure, pulmonary hypertension, and renal hypertension in a subject undergoing dialysis, comprising intradialytically contacting said subject's blood with a thiosulfate-spiked dialysate, wherein an aqueous solution comprising sodium thiosulfate is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0.

In some embodiments, the pulmonary hypertension is neonatal pulmonary hypertension, primary pulmonary hypertension, or secondary pulmonary hypertension.

In one embodiment, the subject is a mammal. In another embodiment, the subject is a human.

In certain embodiments, the methods provided herein return and/or maintain the subject's plasma levels of thiosulfate to normal physiological levels.

In certain embodiments, the embodiments in the remaining paragraphs of this section apply to all methods provided herein.

In one embodiment, the physiological level of thiosulfate in said subject is no more than about 100 micromolar. In another embodiment, the physiological level of thiosulfate in said subject is no more than about 10 micromolar. In yet another embodiment, the physiological level of thiosulfate in said subject is between about 500 nanomolar and about 10 micromolar. In yet another embodiment, the physiological level of thiosulfate in said subject is between about 1 micromolar and about 5 micromolar. In yet another embodiment, the physiological level of thiosulfate in said subject is about 3 micromolar.

In one embodiment, the concentration of thiosulfate in said thiosulfate-spiked dialysate is no more than about 100 micromolar. In another embodiment, the concentration of thiosulfate in said thiosulfate-spiked dialysate is no more than about 10 micromolar. In yet another embodiment, the concentration of thiosulfate in said thiosulfate-spiked dialysate is between about 500 nanomolar and about 10 micromolar. In yet another embodiment, the concentration of thiosulfate in said thiosulfate-spiked dialysate is between about 1 micromolar and about 5 micromolar. In yet another embodiment, the concentration of thiosulfate in said thiosulfate-spiked dialysate is about 3 micromolar.

In some embodiments, the aqueous solution comprising sodium thiosulfate comprises no more than about 10 mg/L, about 50 mg/L, about 100 mg/L, about 150 mg/L, about 200 mg/L, about 250 mg/L, about 300 mg/L, about 350 mg/L, about 400 mg/L, about 450 mg/mL, or about 500 mg/L of sodium thiosulfate.

In some embodiments, the water comprises no more than about 10 mg/L, about 50 mg/L, about 100 mg/L, about 150 mg/L, about 200 mg/L, about 250 mg/L, about 300 mg/L, about 350 mg/L, about 400 mg/L, about 450 mg/mL, or about 500 mg/L of thiosulfate.

In one embodiment, the aqueous solution comprising sodium thiosulfate is added to said unspiked dialysate through a valve that is attached to dialysate tubing at a location before said tubing connects to the dialyzer. In another embodiment, said unspiked dialysate flows through said dialysis tubing at a rate between about 200 mL/min and about 1000 mL/min. In yet another embodiment, said unspiked dialysate flows through said dialysis tubing at a rate between about 300 mL/min and about 900 mL/min. In yet another embodiment, said unspiked dialysate flows through said dialysis tubing at a rate between about 400 mL/min and about 800 mL/min. In yet another embodiment, said unspiked dialysate flows through said dialysis tubing at a rate between about 500 mL/min and about 700 mL/min. In yet another embodiment, said unspiked dialysate flows through said dialysis tubing at a rate about 600 mL/min.

In one embodiment, the aqueous solution comprising sodium thiosulfate is added through the valve to the unspiked dialysate at a rate between about 0 mL/hr and about 750 mL/hr, at a rate between about 50 mL/hr and about 650 mL/hr, at a rate between about 100 mL/hr and about 550 mL/hr, at a rate between about 150 mL/hr and about 450 mL/hr, or at a rate between about 200 mL/hr and about 350 mL/hr. In another embodiment, the aqueous solution comprising sodium thiosulfate is added through the valve to the unspiked dialysate at a rate about 250 mL/hr.

In yet another embodiment, the pH of said thiosulfate-spiked dialysate is between about 7.0 and about 8.0. In yet another embodiment, the pH of said thiosulfate-spiked dialysate is between about 7.1 and about 8.0. In yet another embodiment, the pH of said thiosulfate-spiked dialysate is between about 7.3 and about 8.0. In yet another embodiment, the pH of said thiosulfate-spiked dialysate is between about 7.3 and about 7.5. In yet another embodiment, the pH of said thiosulfate-spiked dialysate is about 7.4.

In yet another embodiment, the said subject is a human with chronic renal failure. In another embodiment, the said subject is a human with acute renal failure.

In yet another embodiment, the said subject undergoes hemodialysis from one to ten times per week. In yet another embodiment, the said subject undergoes hemodialysis from three to seven times per week.

In one embodiment, the thiosulfate-spiked dialysate has less than about 10%, about 9%, about 8%, about 7%, about 6%, about 5%, about 4%, about 3%, about 2%, about 1%, about 0.5%, or about 0.1% decomposition of thiosulfate as reflected by sulfate, sulfide, and sulfite content measured in a sample taken from Detection Point "pre" (100) or Detection point "post" (110).

Methods of Administration

In some embodiments, provided herein are methods for administering sodium thiosulfate to a subject undergoing dialysis, comprising intradialytically contacting said subject's blood with a dialyzer membrane that is also in contact with a thiosulfate-spiked dialysate, wherein an aqueous solution comprising sodium thiosulfate is added to said unspiked dialysate as the unspiked dialysate flows from a dialysis machine to a dialyzer membrane, wherein said unspiked dialysate comprise a mixture of water, an acid concentrate solution, and a bicarbonate concentrate solution, and wherein said thiosulfate-spiked dialysate has a pH greater than about 7.0.

In some embodiments, further provided herein are methods for administering sodium thiosulfate to a subject undergoing hemodialysis, comprising intradialytically contacting said subject's blood with a thiosulfate-spiked dialysate, wherein an aqueous solution comprising sodium thiosulfate is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0.

In one embodiment, the thiosulfate-spiked dialysate has less than about 10%, about 9%, about 8%, about 7%, about 6%, about 5%, about 4%, about 3%, about 2%, about 1%, about 0.5%, or about 0.1% decomposition of thiosulfate as reflected by sulfate, sulfide, and sulfite content measured in a sample taken from Detection Point "pre" (100) or Detection point "post" (110).

Combination Therapy

In some embodiments, the sodium thiosulfate provided herein may also be combined or used in combination with other therapeutic agents useful in the treatment and/or prevention of the diseases and conditions provided herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein) can be administered prior to (e.g., about 5 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks before), concomitantly with, or subsequent to (e.g., about 5 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks after) the administration of a second therapy (e.g., a prophylactic or therapeutic agent) to the subject. Triple therapy is also contemplated herein.

As used herein, the term "synergistic" includes a combination of the sodium thiosulfate provided herein and another therapy (e.g., a prophylactic or therapeutic agent) which has been or is currently being used to treat, prevent, or manage a disease or disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

The sodium thiosulfate provided herein can be administered in combination or alternation with another therapeutic agent. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

The sodium thiosulfate provided herein can be administered in combination with other classes of compounds, including, but not limited to, endothelin converting enzyme (ECE) inhibitors, such as phosphoramidon; thromboxane receptor antagonists, such as ifetroban; potassium channel openers; thrombin inhibitors, such as hirudin; growth factor inhibitors, such as modulators of PDGF activity; platelet activating factor (PAF) antagonists; anti-platelet agents, such as GPIIb/IIIa blockers (e.g., abciximab, eptifibatide, and tirofiban), P2Y(AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopeptidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-adrenergic agents; beta-adrenergic agents, such as carvedilol and metoprolol; antiarrhythmic agents; diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiazolidinediones (e.g., troglitazone, rosiglitazone, and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, and vardenafil); protein tyrosine kinase inhibitors; antiinflammatories; antiproliferatives, such as methotrexate, FK506 (tacrolimus), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone antagonists, and octreotide acetate; microtubule-disruptor agents, such as ecteinascidins; microtubule-stabilizing agents, such as pacitaxel, docetaxel, and epothilones A-F; plant-derived products, such as vinca alkaloids, epipodophyllotoxins, and taxanes; and topoisomerase inhibitors; prenyl-protein transferase inhibitors; and cyclosporins; steroids, such as prednisone and dexamethasone; cytotoxic drugs, such as azathioprine and cyclophosphamide; TNF-alpha inhibitors, such as tenidap; anti-TNF antibodies or soluble TNF receptor, such as etanercept, rapamycin, and leflunimide; cyclooxygenase-2 (COX-2) inhibitors, such as celecoxib and rofecoxib; and miscellaneous agents such as, sodium nitrite, hydroxyurea, procarbazine, mitotane, hexamethylmelamine, gold compounds, low-molecular weight medications, low-molecular weight vitamins, and platinum coordination complexes, such as cisplatin, satraplatin, and carboplatin.

The sodium thiosulfate provided herein can be administered in combination with other solutes that are naturally present in human blood including copper, fluoride, iodine, iron, manganese, magnesium, nitrite, phosphorus, selenium, and zinc.

The disclosure will be further understood by the following non-limiting examples.

EXAMPLES

As used herein, the symbols and conventions used in these experiments, processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); μL, (microliters); mM (millimolar); μM (micromolar); nM (nanomolar); mmol (millimoles); eq. (equivalent); hr or hrs (hours); min (minutes).

For all of the following experiments and the following example, standard work-up and purification methods known to those skilled in the art can be utilized. Unless otherwise indicated, all temperatures are expressed in ° C. (degrees Centigrade). All reactions conducted at room temperature unless otherwise noted. Methodologies illustrated in the following examples are intended to exemplify the applicable chemistry through the use of specific examples and are not indicative of the scope of the invention.

Stability Experiments

Results of the following stability experiments (Example 1 to 4) exemplify the instability of thiosulfate in aqueous solution when acid is added and also the instability of thiosulfate when mixed with a solution comprising an acid concentrate solution and a bicarbonate concentrate solution in the preparation of a dialysate for dialysis.

Concentration of thiosulfate in samples was assayed by ion chromatography. The ion chromatograph was equipped with an electrochemical conductivity detector and a Dionex IonPacAS12A analytical column. The sodium thiosulfate content in the samples tested was calculated against an external sodium thiosulfate standard. USP Sodium Thiosulfate Reference Standard (Item Number 1615107) was the testing standard (United States Pharmacopeia. Rockville, Md.).

Example 1

The material safety data sheet for sodium thiosulfate indicates that the chemical decomposes on contact with acid (Material safety data sheet accessed online at http://www-.thiosulfate.info/downloads/sodiumthiosulfate_msds.pdf).

Example 1 was performed to determine the stability of sodium thiosulfate in an aqueous solution when acid is added. A 60 mg sample of sodium thiosulfate was transferred into a 50 mL volumetric flask. 2 mL of 0.1 N hydrochloric acid was added to the flask. The flask was capped and heated at 80° C. for approximately 24 hours. The flask was subsequently cooled to ambient temperature. 2 mL of 0.1 N sodium hydroxide was added to neutralize the acid, and deionized water was added to bring the volume to 50 mL. The percentage of thiosulfate degradation in this sample was 28.6%. Consistent with published information about the reaction between acid and thiosulfate (available online at https://www.quora.com/Why-does-sodium-thiosulphate-react-with-hydrochloric-acid), this result confirms that sodium thiosulfate decomposes when exposed to acid.

Example 2

Example 2 was performed to determine the stability of sodium thiosulfate in dialysate bicarbonate concentrate solution. At room temperature, 12500 mg sodium thiosulfate (50 mL of 250 mg/mL solution) was added to 7,700 mL of dialysate bicarbonate concentrate solution. The thiosulfate concentration of the dialysate bicarbonate concentrate solution was analyzed by ion chromatography 1) before addition of sodium thiosulfate; 2) 5 minutes after the addition of sodium thiosulfate; and 3) 2 hours after the addition of sodium thiosulfate. The results presented in Table 1 and Table 2 show that thiosulfate is stable when added to dialysate bicarbonate concentrate solution since the concentration of sodium thiosulfate did not decline over time and the concentrations of degradation products sulfate, sulfite, and sulfide did not increase over time.

TABLE 1

Sodium Thiosulfate Concentration in Dialysate Bicarbonate Concentrate

| Sample | Expected Sodium Thiosulfate Concentration | Measured Sodium Thiosulfate Concentration | % Recovery |
| --- | --- | --- | --- |
| Dialysate Bicarbonate Concentrate Solution | 0 | None Detected | NA |
| Dialysate Bicarbonate Concentrate + Sodium Thiosulfate after 5 Minutes | 1.61 mg/mL | 1.65 mg/mL | 102% |
| Dialysate Bicarbonate Concentrate + Sodium Thiosulfate Solution after 2 Hours | 1.61 mg/mL | 1.65 mg/mL | 102% |

TABLE 2

Sulfate, Sulfide, and Sulfite Concentrations in Dialysate Bicarbonate Concentrate + Sodium Thiosulfate

| Sample | Sulfate Concentration (μg/mL) | Sulfite Concentration (μg/mL) | Sulfide Concentration (μg/mL) |
| --- | --- | --- | --- |
| Dialysate Bicarbonate Concentrate Solution | 3.7 | 4.4 | <2.5 μg/mL |
| Dialysate Bicarbonate Concentrate + Sodium Thiosulfate after 5 Minutes | 4.4 | 5.9 | <2.5 μg/mL |

TABLE 2-continued

Sulfate, Sulfide, and Sulfite Concentrations in Dialysate
Bicarbonate Concentrate + Sodium Thiosulfate

| Sample | Sulfate Concentration (μg/mL) | Sulfite Concentration (μg/mL) | Sulfide Concentration (μg/mL) |
|---|---|---|---|
| Dialysate Bicarbonate Concentrate + Sodium Thiosulfate Solution after 2 Hours | 4.3 | 5.4 | <2.5 μg/mL |

Example 3

Example 3 was performed to further determine the stability of thiosulfate in the mixture of sodium thiosulfate and dialysate bicarbonate concentrate solution from Example 2 when mixed with an acid concentrate solution within a dialysis machine. A dialysis machine mixed the dialysate bicarbonate concentrate solution (with sodium thiosulfate added from Example 2), an acid concentrate solution and purified water as the dialysis machined mixes dialysate in clinical practice, with the dilution ratio of 1 part of the acid concentrate solution, 1.72 parts of the bicarbonate concentrate solution, and 42.38 parts of purified water. The dialysis machine used for this experiment was a Fresenius 2008K hemodialysis machine (Fresenius Medical Care, Waltham, Mass.). The machine was primed in bypass mode (dialysate and ultrafiltration rates set at zero) using normal saline. After priming, the hemodialysis machine was run in "Therapy Mode" with the following settings: blood flow rate 300 mL/minute, dialysate flow rate 600 mL/minute, ultrafiltration rate 0 mL/minute, and ultrafiltration time 25 minutes. A sample of the mixed dialysate was collected as it exited the dialysis machine and analyzed by ion chromatography.

The results presented in Table 3 show that thiosulfate in the dialysate bicarbonate concentrate solution almost completely decomposed in the process of mixing with an acid concentrate solution within the dialysis machine.

TABLE 3

Thiosulfate Concentration in Dialysate after
Mixing within Hemodialysis Machine

| Sample | Expected Thiosulfate Concentration | Thiosulfate Concentration by Assay | % Recovery |
|---|---|---|---|
| Mixed Dialysate + Sodium Thiosulfate | 0.0608 mg/L | 0.001824 | 3% |

Example 4

Example 4 was performed to determine the stability of thiosulfate when sodium thiosulfate is added to the dialysate after the dialysate has been prepared within a Fresenius 2008K hemodialysis machine (Fresenius Medical Care, Waltham, Mass.). Dialysate bicarbonate concentrate solution was prepared by adding 1 package of Centrisol® MB-330 Series Sodium Bicarbonate Concentrate powder (650 g) to 7.7 liters of purified water.

The hemodialysis machine mixed the bicarbonate concentrate solution and acid concentrate solution with the dilution ratio of 1 part of an acid concentrate solution, 1.72 parts of a bicarbonate concentrate solution, and 42.38 parts of purified water. The machine was primed in bypass mode (dialysate and ultrafiltration rates set at zero) using normal saline. After priming, the hemodialysis machine was run in "Therapy Mode" with the following settings: blood flow rate 300 mL/minute, dialysate flow rate 600 mL/minute, ultrafiltration rate 0 mL/minute.

An aqueous solution of sodium thiosulfate was prepared by dissolving 25 mg of sodium thiosulfate in 1 liter of purified water. This sodium thiosulfate solution complied with the AAMI quality specification for sulfate (and thiosulfate) since the resulting sodium thiosulfate solution had a thiosulfate anion concentration of approximately 17.72 mg/L. The sodium thiosulfate solution was infused directly into dialysate tubing between the hemodialysis machine and the dialyzer via a valve (Fresenius Dialysate Sample Valve: part #650993) using an Alaris® IV Infusion Pump (Model 8100, CareFusion, San Diego, Calif.). This valve was placed in the dialysate tubing approximately eight inches upstream of the dialyzer (pre-filter). Two sampling ports were placed four inches upstream (pre-dialyzer sampling port) and ten inches downstream (post-dialyzer sampling port) from the dialyzer to collect samples of dialysate for thiosulfate assay by ion chromatography.

The infusion pump infused the sodium thiosulfate solution into the tubing through the valve at a rate of 250 mL/hour (4.16 mL/minute).

Normal saline flowed into the dialyzer at a rate of 300 mL/minute from the Arterial line and exited the dialyzer through the Venous line. Samples of saline were collected from the venous side of the dialyzer.

The results presented in Table 4 show that thiosulfate is stable when a sodium thiosulfate solution mixed with dialysate within dialysate tubing when infused into the tubing at a location that is between the hemodialysis machine and the dialyzer membrane.

TABLE 4

Thiosulfate Concentration in Dialysate Before and After Sodium
Thiosulfate Solution is Added to Dialysate within Dialysate Tubing
Before Dialysate Contacting the Dialyzer Membrane

| Sample | Thiosulfate Concentration* Before the Addition of Sodium Thiosulfate (Time = 0 Min) | Thiosulfate Concentration* After the Addition of Sodium Thiosulfate (Time = 60 Min) |
|---|---|---|
| Dialysate + Sodium Thiosulfate Solution (Before Dialyzer) | 0 | 4.04 μM |
| Dialysate + Sodium Thiosulfate Solution (After Dialyzer) | 0 | 2.20 μM |
| Saline Solution (After Dialyzer) | 0 | 1.62 μM |

*Average results from two samples

The results presented in Table 4 show that thiosulfate can either pass along or pass through a dialyzer if the thiosulfate is added to the unspiked dialysate from the hemodialysis machine at a location between the hemodialysis machine and the dialyzer membrane.

The example set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method for maintaining physiological levels of thiosulfate in a subject undergoing hemodialysis; preventing myocardial infarction in a subject undergoing dialysis; preventing sudden cardiac death in a subject undergoing dialysis; preventing stroke in a subject undergoing dialysis; preventing cardiovascular disease that is characterized by tissue ischemia in a subject undergoing dialysis; preventing high blood pressure in a subject undergoing dialysis; preventing pulmonary hypertension in a subject undergoing dialysis; preventing renal hypertension in a subject undergoing dialysis; or preventing atherosclerosis in a subject undergoing dialysis, comprising intradialytically contacting said subject's blood with a dialyzer membrane that is also in contact with a thiosulfate-spiked dialysate, wherein an aqueous solution comprising sodium thiosulfate is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said thiosulfate-spiked dialysate has a pH greater than about 7.0, and wherein the concentration of thiosulfate in said thiosulfate-spiked dialysate is no more than about 10 micromolar.

2. The method of claim 1, wherein the physiological level of thiosulfate in said subject is no more than about 10 micromolar.

3. The method of claim 1, wherein the physiological level of thiosulfate in said subject is between about 500 nanomolar and about 5 micromolar.

4. The method of claim 1, wherein the physiological level of thiosulfate in said subject is about 3 micromolar.

5. The method of claim 1, wherein the concentration of thiosulfate in said thiosulfate-spiked dialysate is between about 500 nanomolar and about 5 micromolar.

6. The method of claim 1, wherein the concentration of thiosulfate in said thiosulfate-spiked dialysate is about 3 micromolar.

7. The method of claim 1, wherein said aqueous solution comprising sodium thiosulfate comprises no more than about 300 mg/L of sodium thiosulfate.

8. The method of claim 1, wherein said water comprises no more than about 200 mg/L of thiosulfate.

9. The method of claim 1, wherein said aqueous solution comprising sodium thiosulfate is added to said unspiked dialysate through a valve that is attached to dialysate tubing at a location before said tubing connects to the dialyzer.

10. The method of claim 9, wherein said unspiked dialysate flows through said dialysis tubing at a rate between about 500 mL/min and about 700 mL/min.

11. The method of claim 9, wherein said unspiked dialysate flows through said dialysis tubing at a rate of about 600 mL/min.

12. The method of claim 9, wherein said aqueous solution comprising sodium thiosulfate is added through said valve to said unspiked dialysate at a rate between about 100 mL/hr and about 550 mL/hr.

13. The method of claim 9, wherein said aqueous solution comprising sodium thiosulfate is added through said valve to said unspiked dialysate at a rate of about 250 mL per hour.

14. The method of claim 1, wherein the pH of said thiosulfate-spiked dialysate is between about 7.3 and about 7.5.

15. The method of claim 1, wherein the pH of said thiosulfate-spiked dialysate is about 7.4.

16. The method of claim 1, wherein said subject is a human with chronic renal failure.

17. The method of claim 1, wherein said subject is a human with acute renal failure.

18. The method of claim 1, wherein said subject undergoes dialysis from three to seven times per week.

* * * * *